(12) United States Patent
Adams

(10) Patent No.: US 7,671,091 B2
(45) Date of Patent: Mar. 2, 2010

(54) PENIS ENLARGEMENT

(76) Inventor: Kenneth W. Adams, 15 Christine Crescent, North York, Ontario (CA) M2R 1A4

( * ) Notice: Subject to any disclaimer, the term of this patent is extended or adjusted under 35 U.S.C. 154(b) by 1428 days.

(21) Appl. No.: 10/986,027

(22) Filed: Nov. 12, 2004

(65) Prior Publication Data

US 2005/0065159 A1 Mar. 24, 2005

(51) Int. Cl.
*A61K 31/557* (2006.01)
*A61K 31/47* (2006.01)

(52) U.S. Cl. .................. 514/573; 514/308; 514/304

(58) Field of Classification Search ............... 514/573, 514/304, 308
See application file for complete search history.

(56) References Cited

U.S. PATENT DOCUMENTS

| | | | |
|---|---|---|---|
| 5,708,031 A * | 1/1998 | Scott | 514/573 |
| 6,007,836 A | 12/1999 | Denzer | 424/449 |
| 2001/0014685 A1 | 8/2001 | Lin | 514/304 |
| 2001/0041824 A1 | 11/2001 | Zappala | 600/40 |

FOREIGN PATENT DOCUMENTS

| | | |
|---|---|---|
| DE | 199 19 828 A | 11/2000 |
| EP | 0 992 240 A | 4/2000 |
| EP | 1 136 072 A | 9/2001 |
| WO | WO 97/03675 A | 2/1997 |
| WO | WO 00/13664 A | 3/2000 |
| WO | WO 01/08659 A | 2/2001 |
| WO | WO 02/11729 A | 2/2002 |
| ZA | 9905262 A | 4/2000 |

OTHER PUBLICATIONS

The abstract of Smith et al., Clin. Pharm., 1989; 5(5): 373-84.*
Sharlip, Review Article, International Journal of Impotence Research (1997) 9, 193-195.
Abozeid et al., "Chronic Papaverine Treatment: The Effect of Repeated Injections on the Simian Erectile Response and Penile Tissue". The Journal of Urology, 138:1263-1266 (Nov. 1987).
Hwang et al., "Histopathological Change of *Corpora cavernosa* after Long-Term Intracavernous Injection", Eur Urol, 20:301-306 (1991).

* cited by examiner

*Primary Examiner*—San-ming Hui
(74) *Attorney, Agent, or Firm*—Morgan Lewis & Bockius LLP

(57) ABSTRACT

A method for causing a permanent increase in the length and girth of a male subject's penis, the method comprising treatment comprising the step of (a) administering to the male an effective amount of a vasodilator selected from the group consisting of a vasodilator per se and compositions thereof comprising a pharmaceutically-acceptable diluent or carrier, to induce a cumulative prolonged engorgement of the subject's penis; and (b) repeating step (a) as necessary to cause the increase during the treatment. A potentiator which enhances the effect of the vasodilator may also be used.

38 Claims, No Drawings

PENIS ENLARGEMENT

RELATED APPLICATIONS

This application claims priority from U.S. application No. 60/398,562, filed Jul. 26, 2002, and PCT/CA2003/001139, filed Jul. 25, 2003.

FIELD OF INVENTION

This invention is in the field of penis enlargement.

BACKGROUND OF INVENTION

There are various circumstances under which a male subject may desire the permanent enlargement of the length and/or girth of his penis, in both its flaccid and erect states. Penis enlargement may be desired for medical reasons, for example, if a patient is unable to penetrate during coitus due to an unusually small penis size; for cosmetic reasons; or to improve a person's self-esteem.

There have been many attempts to create a safe and effective means for achieving permanent penis enlargement, including the use of external weights and suction devices. The use of external weights is cumbersome and impractical and produces localized compressive forces that may cause localized ischemia. Furthermore, use of weights often leads to a thinning of the penis and may even impair penis function.

Suction devices are also cumbersome and impractical to wear on a prolonged basis, have limited effectiveness, and pose a number of risks. Suction devices produce localized compressive forces that may cause localized ischemia. Vacuum seals with pressure over 20 mm Hg can obstruct capillary flow and inhibit tissue perfusion. Suction devices often come with warnings that the devices should not be used for periods exceeding 20-30 minutes, which may be insufficient to achieve the desired result. Use of suction devices can also result in the thickening of the skin and accumulation of fluid in the superficial layers of the skin and subdermis. The skin of the penis is hypermobile, and only very loosely connected to deeper connective tissues and structures that comprise the erectile tissues of the penis. The skin of the penis can readily separate from the fibrous connective tissue capsule which encloses the erectile tissue of the penis when externally applied suction forces are applied to the penis.

Also, any suction forces applied to the penis will have a proportionately larger effect on the skin, and the forces on the deeper structures diminish dramatically. The increase in the surface area of the skin causes the suction forces to be applied mainly to the skin, not to the erectile tissue and the surrounding capsule of the cavernosal tissue. As a result, the skin can be thickened as fluid is extravasated and there is typically no, or only a limited enlargement, of the underlying erectile tissues of the penis. Use of suction devices may also cause the separation of the skin from the subdermis and the formation of seromas or blisters on the penis. The application of suction devices to the penis causes the extravasation of red blood cells out of the vascular spaces and into the extracellular compartments. If vacuum devices are applied for extended periods of time, this may lead to a significant pigmentation of the penis. Applying a suction device repeatedly may cause the deposition of large amounts of iron and other hemoglobin degradation products in the tissue of the penis causing hemosiderosis, which ultimately results in fibrosis. Furthermore, erectile dysfunction may result from prolonged use of these devices.

SUMMARY OF THE INVENTION

In a first aspect, this invention provides a pharmaceutical vasodilator which induces a cumulative prolonged engorgement of a human penis, optionally as a composition together with a pharmaceutically-acceptable diluent or carrier, for use in causing a permanent increase in size of the human penis. As explained in greater detail below, the permanent increase in size is achieved by repeated use of the vasodilator or composition thereof, say, once a day for a few days a week over many weeks, possibly many months.

In accordance with another aspect of this invention, there is provided a method of enhancing penis size by administering said vasodilator or composition thereof so as to induce a cumulative prolonged engorgement of the penis. According to the method, such an administration lasts for a limited time during one day, and is repeated up to daily or a few days a week over a period of several weeks.

Thus, in one aspect the invention provides a method for causing a permanent increase in the length and girth of a male subject's penis, said method comprising treatment comprising the step of a (a) administering to said patient an effective amount of a vasodilator selected from the group consisting of a vasodilator per se and compositions thereof comprising a pharmaceutically-acceptable diluent or carrier, to induce a cumulative prolonged engorgement of the subject's penis; and (b) repeating step (a) as necessary to cause said increase during said treatment.

Preferably, the composition includes a pharmaceutically acceptable diluent or carrier, which can aid in the administration of the vasodilator of the composition for inducing a prolonged engorgement of a human penis, for use in causing a permanent enlargement of the penis.

Although it is known in the prior art that vasodilators can be administered to a male to induce engorgement of the penis, the prior art is silent on the period of engorgement. In contrast, the present invention provides for a prolonged period of engorgement as defined herein. Further, in accordance with the practise of the present invention, a permanent increase as defined herein is the primary object of the invention.

The prior art is both silent on the hereindefined period of engorgement and on the resulting permanent increase in penis size. In contrast to the disclosure and teachings of the prior art, in the present invention, engorgement of the penis is not the final desired result, nor in isolation is the required period of engorgement. The present invention defines the nature of the compound and its function, i.e. a vasodilator of use in the present invention, and how it provides the solution of the problem by administration thereof to provide the essential prolonged engorgement feature to effect permanent increase in penis size, through one or more administrative treatments.

This invention provides the use of pharmacological vasodilators to cause a permanent increase in the length and girth of a human penis. As used herein, the term "permanent increase" refers to a long-term increase and refers to an increase that lasts for several months or years, or maybe even the life-time of the person.

The term "penis length" refers to the maximum length of the penis, as measured along the dorsal surface of the penis from the symphysis pubis to the tip or end of the glans penis when the glans penis is pulled manually and put under tension. Preferably, the measurement is taken when the penis is fully erect.

The term "penis girth" refers to the largest measured value obtained for circumference of the erect penis, as measured in the midshaft region (middle third). Preferably, the measurement is taken when the penis is fully erect.

An engorgement is deemed "cumulative prolonged" when an erectile response lasts for at least 3 hours over a 24 hours period. Typically, an engorgement of the invention, one that is suitable to cause penis enlargement, is repeatedly induced for a cumulative period of 3 to 6 hours, daily (or at least four days per week), for weeks or months, but for at least 4 weeks.

Erectile responses may be categorized according to the following: a 100% response or engorgement is a maximal erection which is very hard, firm and unbendable, a 75% response is the softest response considered hard enough for penetration, a 65-75% response would be partially engorged but would not be sufficient for penetration and intercourse, 40-65% is not a usable erection for sexual intercourse but will have therapeutic effect for enlargement according to the invention, and a response of less than 40% is a slightly engorged, very soft penis wherein the size of the penis is close to the non-erect dimension of flaccid penis with no discernable significant firmness when it is manually palpated by an experienced health professional, and is probably not useful for penis enlargement. Therefore, a "cumulative prolonged engorgement" would be an erectile response that is over 40% for a period of at least 3 hours in a 24 hours period.

As used herein, a "full erection", or the term "fully erect", refers to an erectile response of between 75-100%.

The engorgement of the invention is typically for a "cumulative prolonged" period, as described further below. The engorgement period is thus usually at least 3 hours, but may be 3½ hours, 4 hours, 4½ hours, 5 hours, 5½ hours, even up to 6 hours, but heavy engorgement of a penis, say 40% or more, is usually avoided for extended periods of time, i.e., of more than 6 hours. The erectile response may, thus, be of the 3-6 hours engorgement resulting from a single administration per 24 hours or as a result of a plurality of administrations in this 24 hours period.

It is possible, thus, with some patients to obtain the required engorgement for a suitable length of time by administering a single dose. Other patients may require two doses, one at the beginning of a daily treatment, and one or more later one during the same treatment so as to maintain the engorgement, say above 40% engorgement. Multiple dosing also may simply be a preferred method of obtaining and maintaining a suitable degree of engorgement without inducing (or at least inducing for a relatively short period of time) a heavy engorgement of say 75%, 90% or 100%, which the subject may simply want to avoid for personal or other reasons.

Typically, the initial erectile response is at least 65%. Later doses can be administered if the engorgement falls below 65%, or say 40 to 45%.

Administration may be two times a week for one month, more likely 3 or 4 or more days per week, and treatments may to on for several weeks or months, often at least 3 months.

Sometimes an endpoint is chosen after a degree of enlargement is obtained, say 5% (length, and/or girth) within 12 to 18 months, for example. More typically, an increase of say 30% is sought, depending upon the desire of the subject and the effectiveness of the treatment, which can vary.

Accordingly, the daily engorgement can include a 75-100% erectile response for at least 90% of the time of the prolonged engorgement. In another embodiment, the engorgement includes a 75-100% erectile response for 50-90% of the time of the prolonged engorgement time. Alternatively, the engorgement can include a 75-100% erectile response for up to 50% of the time of the prolonged engorgement. Also, engorgement can include a 40-75% erectile response for at least 3 hours.

The active ingredient is a compound which causes vasodilation, e.g., a vasodilator. The vasodilator may be selected from the group consisting of nitrovasodilators, ACE inhibitors, angiotensin receptor antagonists, phosphodiesterase inhibitors, direct vasodilators, adrenergic receptor antagonists, calcium channel blocking drugs, alpha blockers, beta blockers, lymphthomimetics, vitamins, organic nitrates, serotonin receptor-blocking agents, angina blocking agents, other hypertensive agents, cardiac stimulating agents, agents which improve renal, vascular function, sympathomimetic amine, and salts, derivatives, precursors, pharmaceutically active sequences or regions, peptidomimetics, mimetics, and mixtures thereof.

Preferably, the vasodilator is selected from the group consisting of papaverine, chlorpromazine, atropine, phentolamine, and prostaglandin E1, and mixtures thereof. A preferred vasodilator is prostaglandin E1.

Administration can be by direct injection to the cavernosal tissue, by needle, auto-injector, slow sustained injection pump, high pressure injection device, micro pump infustion, urethral suppository, or implantable sustained release drug or device.

The composition can be formulated for systemic administration by oral, sublingual, or suppository administration, intravenous administration by needle, auto-injector, slow sustained injection pump, micro pump infusion, high pressure injection device, or implantable sustained release drug or device, or topical administration, such as through the use of creams, lotions or patches.

The composition can be formulated for administration to the dense connective tissue surrounding the erectile tissue of the penis by a deep injection that goes below the dermis and subcutaneous tissues. The composition can be formulated for administration to the dorsal suspensory ligand of the penis.

A preferred embodiment includes a composition formulated for intracavernosal injection, but the composition might also be formulated for administration by an implantable sustained release drug or device.

Prostaglandin E1 could be administered in a dosage range of from about 0.5 to about 100 micrograms by intracavernosal injection, or systemically at a dosage of 2 to 10,000 micrograms by an implantable sustained release drug or device. In another aspect of the invention, the active agent is combined with a potentiator, either directly or in vivo.

The potentiator can thus be formulated for administration by direct injection to the cavernosal tissue, by needle, auto-injector, slow sustained injection pump, high pressure injection device, micro pump infusion, urethral suppository, or implantable sustained release drug or device, etc.

The composition can be formulated for systemic administration by oral, sublingual, or suppository administration, intravenous administration by needle, auto-injector, slow sustained injection pump, high pressure injection device, micro pump infusion, or implantable sustained release drug or device, or topical administration, such as through the use of creams, lotions or patches.

The potentiator can be formulated for administration to the dense connective tissue surrounding the erectile tissue of the penis by a deep injection that goes below the dermis and subcutaneous tissues.

The potentiator can be formulated for administration to the dorsal suspensory ligand of the penis, or for intracavernosal injection, or for administration by an implantable sustained release drug or device.

The potentiator can be administered separately from the composition or concurrently with the composition.

The pharmaceutical composition can be such that the potentiator is for administration more than once both separately from and concurrently with the composition.

The potentiator can be a hormone. The hormone can be an androgen selected from the group consisting of, but not limited to, the naturally occurring androgens and derivatives thereof, or any agent that will stimulate the androgen receptor directly or indirectly, including androsterone, androsterone acetate, androsterone propionate, androsterone benzoate, androsterone, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone. (DHT; also termed "stanolone"), 17.beta.-hydroxyandrost-4-en-3-one, 5.alpha.-dihydrotestosterone, dromostanolone, dromostanolone propionate, ethylestrenol, nandrolone phenpropionate, nandrolone decanoate, nandrolone ftirylpropionate, nandrolone cyclohexanepropionate, nandrolone benzoate, nandrolone cyclohexanecarboxylate, oxandrolone, stanozolol and testosterone, pharmaceutically acceptable esters of testosterone and 4-dihydrotestosterone, including esters formed from the hydroxyl group present at the C-17 position, including, but not limited to, the enanthate, propionate, cypionate, phenylacetate, acetate, isobutyrate, buciclate, cyclopentylpropionate, isocarponate, heptanoate, decanoate, undecanoate, caprate and isocaprate esters, pharmaceutically acceptable derivatives of testosterone such as methyl testosterone, testolactone, oxymetholone and fluoxymesterone; synthetic androgens, and 7-Methyl-Nortestosterone ("MENT") and its acetate ester, and salts, derivatives, precursors, pharmaceutically active sequences or regions, peptidomimetics, mimetics, and mixtures thereof.

A specific potentiator is the androgen testosterone. Another is 4-dihydrotestosterone.

The potentiator can be selected to promote the elongation of collagen, or to inhibit collagen cross-linkage, or to increase collagen solubility.

The potentiator can be selected from a group consisting of relaxin, insulin like growth factors, growth hormone, metalloproteinases or metallo-proteinase agonists or promoters of collagenase activity, tissue inhibitors of matrix metalloproteinases (TIMPS), other agents that increase collagen solubility, prostaglandins, corticosteroids, potassium aminobenzoate (Potaba™), and dimethyl sulfoxide (DMSO), D-penicillamine, and salts, derivatives, precursors, pharmaceutically active sequences or regions, peptidomimetics, mimetics, and a mixture thereof.

A particular potentiator is relaxin.

A prostaglandin potentiator can be prostaglandin F2 alpha or prostaglandin E2. The potentiator might be relaxin, prostaglandin F2 alpha, or prostaglandin E2, or the biochemical mediators that result in the desired changes in collagen or the connective tissue that produces and remodels collagen and express the effects of relaxin, prostaglandin F2 alpha, or prostaglandin E2.

Another potentiator is aminobenzoate potassium (Potaba™), or dimethyl sulfoxide (DMSO).

Relaxin can be administered at a dosage of 0.02 to 10 micrograms/kg body weight/day by intracavernosal injection. Relaxin might be for topical administration at a dosage of 25 to 400 micrograms/kg body weight/day. The relaxin might be for administration at a dosage of 0.02 to 1 micrograms/kg body weight/day by injection into the dense connective tissue surrounding the erectile tissue of the penis.

A device can be used to prolong the retention of the composition in the penis. For example, a ring designed to fit around the base of the penis might be used.

Thus, as hereinabove defined, the invention provides a method for causing enlargement of a male subject's penis, comprising the steps of (a) administering to the patient an effective amount of a pharmaceutical vasodilator, optionally in admixture with a pharmaceutically acceptable agent to induce a prolonged engorgement of the subject's penis; and (b) repeating step (a) as necessary to cause said enlargement.

The invention includes a kit that include a composition of the invention as disclosed herein, in combination with instructions for administering the composition to a human male according to a method disclosed herein for the purposes disclosed herein.

Typically, such instructions are provided in written form, but they could be provided orally by a health professional, or in an electronic form on a medium such as a video compact disc, laser-readable disk, video tape, audio tape or disk, etc.

DETAILED DESCRIPTION OF THE INVENTION

In one embodiment of the invention, a pharmaceutical vasodilator composition is administered to a male patient to cause a prolonged engorgement of the penis in order to cause expansion of the erectile tissue. The pharmaceutical composition comprises a pharmaceutically acceptable vasodilator for causing a prolonged suitable engorgement of the penis, together with a pharmaceutically acceptable diluent or carrier. The vasodilator may be a drug typically used to treat erectile dysfunction, but administered at a similar or higher dosage or sequentially as two or more lesser doses to achieve a prolonged period of engorgement followed by an additional period of lesser engorgement. Optionally, the agent may be administered at a slow rate with a micro infusion pump, time-release device or other self-injection technique or device. During a treatment, the penis should be engorged for a minimum of 3 hours and typically there is one treatment per day, and at least four treatments per week.

A very hard firm erection which is usually preferred for erectile dysfunction will have more veno-occlusive obstruction of the circulation and the reduced flow of fresh oxygenated blood into the erectile tissue will limit the maximum duration that the erection can be safely maintained. A softer less firm response can be safely and comfortably maintained for a greater length of time than a full erection.

The vasodilator drug may be one which either directly or indirectly causes vasodilation and may be classified, without limitation, in one of the following categories, namely, nitrovasodilators, ACE inhibitors, angiotensin receptor antagonists, phosphodiesterase inhibitors, direct vasodilators, adrenergic receptor antagonists, calcium channel blocking drugs, alpha blockers, beta blockers, lymphthomimetics, vitamins, organic nitrates, serotonin receptor-blocking agents, angina blocking agents, other hypertensive agents, cardiac stimulating agents, agents which improve renal, vascular function, sympathomimetic amine and mixtures thereof. For example, the drug may be any suitable vasodilator, such as papaverine, chlorpromazine, atropine, phentolamine, and prostaglandin E1, and salts, derivative, precursors, pharmaceutically active sequences or regions, peptidomimetics, mimetics, and mixtures thereof. Other drugs which may cause vasodilation include, without limitation, any of the following: niacin, nitroglycerine, nilatrin hydrochloride, pentoxyphylene, phenoxybenzamine, dichlophenac, hydralazine, hydrazaline, hydrochlorothiazide, sodium nitroprusside, isoxaprine hydrochloride, epoprostenol sodium, nylidrin hydrochloride, tolazoline hydrochloride, nicotinyl alcohol, phentolamine mesylate, phentolamine hydrochloride, yohimbine, thymoxamine imipramine, verapamil, isoxsuprine, naftidrofuryl, tolazoline, hydroisosorbide, dibenamine dinitrate, captopril, enalapril, enalaprilat, quinapril, lisinopril, ramipril, losartan, amrinone, milrinone, vesnarinone, nicorandil, prazosin, labetalol, celiprolol, carvedilol, bucindolol, nifedipine, dobutamine, minoxidil, nylidrin, and salts, derivatives, precursors, and mixtures thereof. Preferably, the vasodilator is prostaglandin E1, alone or with other vasodilators, administered as one or more doses that are typically lower than what would be used to treat erectile dysfunction. For example, the prostaglandin E1 may be administered by intracavernosal injection in a dosage range of 0.2 mcg to 500 mcg, more preferably in a dosage range of 0.5 mcg to 100 mcg. For example again, the prostaglandin E1 may be administered by an implantable sustained release drug or device in a dosage range of 0.5 mcg to 20,000 mcg, more preferably in a dosage range of 2 to 10,000 mcg (mcg=microgram).

Optionally, the patient may be treated with an additional, second pharmacological agent, to potentiate the effect of the composition which causes a prolonged, engorgement of the penis. Here, the second agent is called a "potentiator". The potentiator may be administered as part of the composition, separately from the composition, or a combination of both.

The potentiator may be a pharmacological agent or combination of agents that promote cellular processes that result in biological and/or mechanical creep and ultimately induce remodelling of the connective tissues that help define the size and shape of the penis. In addition, an agent which increases solubility of collagen may be used as a potentiator. Agents with very specific mechanisms of action may be used, or other agents with pleomorphic mechanisms of action, such as relaxin or growth hormone which trigger diverse mechanisms to induce growth in the penis may be used. For example, agents may be administered that facilitate the elongation of collagen fibres and accelerate the turnover remodelling rates of collagen through numerous mechanisms. For example, D-penicillamine and dimethyl sulfoxide (DMSO), which promote the elongation of collagen by inhibiting or interfering with inter- and intramolecular collagen cross-linkage may be used. Other agents include, but are not limited to, relaxin, insulin like growth factors, growth hormone, metalloproteinases or metalloproteinases agonists or promoters of collagenase activity, tissue inhibitors of matrix metalloprotenases (TIMPs) other agents that increase collagen solubility, prostaglandins, corticosteroids, or aminobenzoate potassium, a commercial brand being known as Potaba™. Preferred prostaglandins are prostaglandin F2 alpha and prostaglandin E2. Also included are pharmaceutically active sequences, peptidomimetics, or mimetics above the above-listed molecules.

Relaxin directly and indirectly triggers a cascade of complex biochemical and cellular effects that can cause general morphological changes to genitalia. Prostaglandins such as prostaglandin F2 alpha and prostaglandin E2 have similar effects. This invention includes the mediators of these cascades as potentiators.

Collagen is a component of the extracellular matrix (ECM), which is a dynamic entity with many other components (e.g., proteoglycans, fibronectin, elastin, laminin, etc.) that functions as a storage reservoir for cytokines and enzymes and interacts intimately with surrounding cells to provide a structural scaffold and an efficient biochemical communication network within tissues. Enzymes primarily responsible for ECM remodeling are the Matrix MetalloProteinases (MMPs), which break down ECM components, and the Tissue Inhibitors of Matrix MetalloProteinases (TIMPs). Maintenance of a balance of ECM synthesis and MMP/TIMP activity in tissues is required for normal homeostasis; imbalances will generally lead to diseases or developmental problems such as scleroderma, periodontal disease, restenosis, osteoarthritis, liver cirrhosis, glomerulonephritis, and ulceration.

Relaxin is a 6 kDa peptide hormone that is structurally similar to insulin; the prohormone form consists of B-C-A chains (20 kDa), and the C chain is proteolytically excised in 'mature' relaxin. However, unlike many other pro-hormones, pro-relaxin retains its biological activity. The profile of conserved amino acid sequences among various species such as pig, human, whale, porpoise, and shark suggests that relaxin is an ancient hormone with a unique molecular evolutionary history. The most recognized effect of relaxin on target cells is induction of MMP expression and inhibition of collagen synthesis.

Historically, relaxin has been classified as a "pregnancy hormone" that acts on reproductive tissues only during pregnancy, preparing the female for parturition by "relaxing" the pelvic ligaments and tendons. However, recent evidence suggests that relaxin may be classified as a "master hormone" that also induces biochemical, changes in a number of non-reproductive tissues. In addition to up-regulating MMP expression in reproductive tissues such as the cervix and placenta relaxin up-regulates expression of MMP-1 and MMP-3 in lung fibroblasts, skin fibroblasts, and fibrocartilaginous cells. Relaxin receptors are found in the brain heart, skin, nipples, small intestine, mammary gland, blood vessels, and testes. The bioactivity of relaxin is unique when compared with other cytokines that affect ECM remodeling.

The potentiator or potentiators may be administered as part of the composition, separately from the primary composition, or a combination of both. For example, the potentiator Potaba™ may be administered orally and the composition administered intracavernosally. Optionally, the potentiater may be administered locally into the cavernosal tissue, externally but adjacent the cavernosal tissue by injection into the surrounding connective tissue or the dorsal suspensory ligament of the penis, or a combination. The potentiator may be an agent which activates the androgen receptor, which is involved with male sexual development and function. For example, the potentiator may be an androgen hormone such as, but not limited to, the naturally occurring androgens and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 17.beta.-hydroxyandrost-4-en-3-one, 5.alpha.-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone and testosterone esters, such as testosterone enanthate, testosterone propionate and testosterone cypionate, may be used. The aforementioned testosterone esters are commercially available or may be readily prepared using techniques known to those skilled in the art or described in the pertinent literature.

The aforementioned androgenic agents are selected from the group consisting of naturally occurring androgens, synthetic androgens, and derivatives thereof, and any agent that will stimulate the androgen receptor directly or indirectly. The active agents may be incorporated into the present dosage units and thus administered in the form of a pharmaceutically acceptable derivative, analog, ester, salt, or amide, or the agents may be modified by appending one or more appropriate functionalities to enhance selected biological properties such as penetration through mucosal tissue. Preparation of esters, as noted in the preceding section, involves functionalization of hydroxyl and/or carboxyl groups that may be present, as will be appreciated by those skilled in the arts of pharmaceutical chemistry and drug delivery. For example, to prepare testosterone esters, the 17-hydroxyl group of the testosterone molecule is generally caused to react with a suitable organic acid under esterifying conditions, such conditions typically involving the use of a strong acid such as sulfuric acid, hydrochloric acid, or the like, and a temperature sufficient to allow the reaction to proceed at reflux. Esters can be reconverted to the free acids, if desired, by using conventional hydrogenolysis or hydrolysis procedures.

Testosterone is the principal steroid secreted by the testes and is the primary circulating androgen found in the plasma of males. Testosterone is converted to 4-dihydrotestosterone (DHT) by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT"') and its acetate ester.

Optionally, a mechanical device such as a ring may be used at the base of the penis to prolong retention of the composition within the penis. The mechanical device may also be used to prolong retention of any pharmacological agent used to potentiate the effect of the composition, i.e., the potentiator.

The pharmaceutical composition is administered to the patient in a pharmaceutically acceptable dosage and schedule of administration to achieve engorgement which lasts for several hours. The treatment regimen typically begins with the physician determining a first dosage amount to try on a patient to determine that subject's erectile responsiveness to the composition. The amount of the first dosage given will be determined, among other things, by the route of intended administration, the age of the man, the recent history of erectile function of the man, and pre-existing health conditions of the man.

To achieve an erectile response, one or more doses may be administered which are typically of similar or a higher amount than that used to treat erectile dysfunction. This should produce a full erection. Alternatively, two or more lesser doses may be administered to achieve a prolonged engorgement of about 40-75% response. Optionally, a combination of similar, higher, and lesser doses may be administered.

It is the duration of a full erection and the subsequent period of engorgement that determines the starting dose. The penis may be visually inspected and palpated to determine the extent of the response to the composition.

A desirable first erectile response for the purposes of this invention is considered to be at least a 45-100% response for a period of at least two hours, but preferably 3-6 hours duration. For intracavernosal injections, first dosage amounts may range from about 0.5 mcg to about 30 mcg of prostaglandin E1, and more preferably from 1 mcg to 6 mcg. If a 70-100% erection is not achieved within 20 minutes of the first test dosage amount administered by intracavernosal injection, a second injection of less, the same or more of the composition as the initial test injection, depending on if there was any response with the first test dosage. For example, if there was a 55-70% response, a "booster" shot of a lesser amount than the first dosage amount may be administered. If there was no response, the same or more than the amount of the first dosage amount may be administered. Other administrative routes may take a longer or shorter time to achieve the initial response. The dosage is gradually increased by an amount that is usually within 50% to 200% the previously administered dosage until a satisfactory response is achieved. Using these general guidelines a maximum of two injections are administered per visit.

If an erection is not achieved with the first or second injection, one or more additional appointment/visits on another day may be required to establish the dose.

Once the correct response is achieved, it will be followed by one or more confirmatory doses on subsequent visits. Once a starting dosage amount of a single or a sequence of two or more injections is established that provides a response of suitable duration, the dosage may be titrated, for example, to provide the subject with an initial 70%-100% engorgement followed by a further period of reduced engorgement of at least 40% for at least 3-6 hours. The firmness of the penis generally decreases over this period, but will be at least 40% engorged for at least 3 and preferably up to 6 hours and less than 75% engorged for the majority of the time.

Depending on the subject's response to the treatment, higher dosages may be used as determined by the physician. However, it should be noted that higher dosages may increase the risk of a very firm erection that may cause ischemia. If the veno-occlusive mechanism closes to an extent that it reduces the inflow of fresh oxygenated blood for a sufficient period to cause pain and tissue damage it can cause a medical condition called a priapism. The risk of priapism can be reduced by using smaller multiple doses. The subject's condition should be monitored and the dosage adjusted to ensure that the patient experiences a prolonged period of engorgement, rather than a prolonged full erection, which may lead to priapism and associated health complications.

Subjects should have careful instruction in the signs and symptoms of priapism, and have access to 24 hour emergency medical treatment to allow prompt treatment and eliminate any risks of ischemia to the penis.

A physician should closely monitor the subject's response to medication, to determine signs of edema, tenderness, and other early signs that the dose is excessive and needs adjusting.

If lumps or unexpected thickening of the penis occurs during treatment, the patient may have to stop or suspend treatment for a period of time. Once the appropriate dosage for a given patient has been determined, the treatment may be self-administered under the close supervision of a properly trained physician or health professional.

The treatment is repeated over a period of time sufficient to cause a permanent increase in the length and girth of the patient's penis. The treatment may comprise administration with the composition alone, or in conjunction with potentiator. For example, the treatment may be repeated daily or at least two times a week over a period of several weeks or at least one month. More preferably, the treatment may be repeated at least 3-4 times a week for a period of at least 3 months. For treatment periods of between 12 and 18 months, an increase of at least 5% may be achieved in the length and girth of an erect penis, and increases of at least 30% or even at least 50% in the length and girth of an erect penis may be achieved. Active treatment for more extended periods, e.g. 24 months, may yield greater results.

The subject may continue with normal sexual activities during the course of treatment. In fact, due to the prolonged elevation in penile blood flow, patients using this treatment will experience a very significant increase in erectile function. During treatment, patients will have dramatic improvements in the frequency, strength and duration of their own naturally stimulated erections. Men using this treatment will require much lower levels of sexual arousal and stimulation to produce and maintain their own naturally induced erections.

The pharmaceutical composition and/or potentiator may be administered using a variety of different methods known to those of skill in the art, including administration by direct manual injection to the cavernosal tissue by needle, auto-injector, slow sustained injection pumps, high pressure injection devices, urethral suppository, implantable sustained release drug or device, microinfusion pump or systemically by oral administration, parenteral administration such as subcutaneously or intra muscularly, intravenous administration by needle, auto-injector, slow sustained injection pump, high pressure injection device or implantable sustained release drug device, or topical administration, such as through the use of creams, lotions or patches with suitable additives for transdermal delivery. Most conveniently, the treatment with the vasodilators is administered by intracavernosal injection. Optionally, the pharmaceutical composition and/or potentiator may be administered by a deep injection that is well below the dermis and subcutaneous tissues which is administered into the dense connective tissue that surround the erectile tissue of the penis. This may be in the form of a depot oil. The pharmaceutical composition and/or potentiator may also be administered to the dorsal suspensory ligand of the penis.

For example, relaxin may be administered by intracavernosal injection at a dosage ranging from 0.01 to 50 mcg/kg body weight/day, more preferably at a dosage ranging from 0.02 to 10 mcg/kg body weight/day, or topically at a dosage ranging from 5 to 1000 mcg/kg body weight/day, more preferably at a dosage ranging of 25 to 400 mcg/kg body weight/day, or by injection into the dense connective tissue surrounding the erectile tissue of the penis at a dose ranging from 0.01 to 50 mcg/kg body weight/day, more preferably at a dosage ranging from 0.02 to 10 mcg/kg body weight/day, and more preferably still, at a dosage ranging from 0.02 to 1 mcg/kg body weight/day.

Kits of the composition are part of this invention. The kit may include a pharmaceutical composition of the invention and written instructions as to how and when to administer the composition in order to achieve an enlarged penis by repeated treatments, over a period of weeks or months. Optionally, the kit may include a pharmaceutical composition of the invention with written and possibly videotaped/cd rom (compact disc) video instructional information and/or be accompanied by oral instructions from a health professional as to how and when to administer the composition in order to achieve an enlarged penis. Preferably, the patient does not self-administer the composition without the supervision of a health professional. Optionally, the kit may also include an agent which will potentiate the effects of the pharmaceutical compositions of this invention. In this case, written, video format instructions or oral instructions will be included as to how to use the agent to potentiate the effect of the composition.

Without binding itself to any particular theory, applicant believes that this invention works by inducing biological creep (induction of cellular processes for tissue remodelling and cellular growth) and, to a lesser degree, biomechanical creep (mechanical microscopic tearing and viscoelastic stretching of the connective tissue). The pharmaceutical composition of the present invention induces prolonged penile engorgement, which results in a significant increase in the arterial blood flow through the penis. This increase in blood flow can safely activate the veno-occlusive mechanism that then expands and pressurizes the erectile tissue for several hours, while providing a constant flow of fresh oxygenated blood flow into the penis. This avoids the complications and health risks caused by priapism and ischemia and safely applies prolonged, continuous stimulation of the cellular processes necessary to induce maximal rates of biological and mechanical creep to enlarge the penis with minimal distortions in the shape or architecture of the penis. The potentiators may be co-comittently administered to accelerate the rate of the cellular processes that remodel the tissues of the penis in the growth/enlargement process.

In order that the invention may be better understood, preferred embodiments will now be described in the following examples.

EXAMPLE 1

A male patient, age 41, was treated with intracavernosal injections of a vasodilator, prostaglandin E1, on a regular basis (approximately four to five times per week) over an 18 month treatment period. A sufficient quantity was administered to maintain a prolonged engorgement of an erectile response between 40-75% over a period of several hours, generally 3 to 6 hours. The quantity of medication was adjusted from time to time in accordance with the patient's response, which was monitored at least weekly.

The size of the patient's fully erect penis increased from 5.8 inches to 8.6 inches in length (about an 48% increase) and 3.7 inches to 5.8 inches in girth (about an 56% increase) over the 18-month treatment period. Following the discontinuation of this treatment, the erect penis length remained stable for two years at over 8½ inches. Treatment was re-instituted combining intracavernosal injections 3-4 times per week of a mixture of testosterone (0.5 mg) and vasodilators with low dose oral Potaba (500-1000 mg) 3-4 times per day. After a short treatment period of 2½ months, the patient's erect penis was over 9 inches in length, which means he has gained an additional 0.4-0.5 inches in length (about an 6% increase). The total increase in length was therefore about 3.2 inches (about an 55% increase) in length.

EXAMPLE 2

A male patient, age 30, was treated with intracavernosal injections of the vasodilator on a regular basis (approximately four to five times per week) over a 6-month treatment period. A sufficient quantity was administered to maintain a prolonged engorgement over a period of about 3 to 6 hours. The quantity of medication was adjusted in accordance with the patient's response. The potentiator potaba (aminobenzoate) (1000 mg/4 times per day) was administered orally to the patient for the last 60 days of treatment.

The patient's erect penis increased from 5.6 inches to 7.7 inches (about an 38% increase) in length and 3.2 inches to 5.3 inches (about an 65% increase) in girth over the 6-month treatment period.

EXAMPLE 3

A male patient, age 52, was treated with separate intracavernosal injections of vasodilators, Papavarine, phentolamine and prostaglandin E1, on a regular basis, selected from treatments of 0 to 4 times per week, over a 7 month treatment period along with daily subcutaneous injections of a prostaglandin F analogue. A sufficient quantity of vasodilator was administered to maintain a prolonged engorgement of an erectile response greater than 70% for 3.5-5 hours duration. The quantity of medication was adjusted from time to time in accordance with the patient's response, which was monitored initially weekly then monthly once the patient had mastered the IC technique and the responses were consistently of the same duration.

The size of the patient's fully erect penis increased from 5.0 inches to 6.3 inches in length, i.e. about a 26% increase, over the 7-month treatment period. Following the discontinuation of this treatment, the erect penis length remained stable.

EXAMPLE 4

A male patient, age 34, was treated with intracavernosal injections of a triple mix of the vasodilators Atropine, Chlorpromazine and Papavarine on a regular basis (approximately two to five times per week) over a 4-month treatment period. A sufficient-quantity was administered to maintain a prolonged engorgement of 60-90% over a period of about 3 to 4.5 hours. The quantity of medication was adjusted in accordance with the patient's response. The potentiator, Potaba™—potassium aminobenzoate (1000 mg/3-4 times per day) was administered orally starting 1 month before starting the IC injections of the vasodilators Atropine, Chlorpromazine and Papavarine.

After 5 months of treatment the patient's erect penis increased from 6.0 inches to 7.1 inches (about an 18% increase) in length.

EXAMPLE 5

A male patient, age 44, was treated with intracavernosal injections of a quadruple mix of the vasodilators prostaglandin E1, Atropine, Chlorpromazine and Papavarine on a regular basis (approximately two to four times per week) over a 4-month treatment period. A sufficient quantity was administered to maintain a prolonged engorgement over a period of about 3 to 5 hours. The quantity of medication was adjusted in accordance with the patient's response. The potentiator dihydrotestosterone 5% ointment was administered orally starting two weeks before starting the IC injections of the vasodilators Atropine, Chlorpromazine and Papavarine and prostaglandin.

After 4 months of treatment the patient's erect penis increased from 5.2 inches to 6.5 inches (about a 25% increase) in length.

EXAMPLE 6

A male patient, age 44, was treated with intracavernosal injections of the vasodilator phentolamine on a regular basis (approximately two to four times per week) over a 4-month treatment period. Phentolamine was frequently combined with indirect vasodilating effects of oral Viagra to produce and maintain a prolonged engorgement of 60-90% over a period of about 3 to 5 hours. The quantity of medication was adjusted in accordance with the patient's response. The potentiator dihydrotestosterone gel was administered orally starting two weeks before starting the IC injections of the vasodilators Atropine, Chlorpromazine and Papavarine and prostaglandin.

After 4 months of treatment the patient's erect penis increased from 5.2 inches to 6.5 inches (about a 25% increase) in length.

EXAMPLE 7

A male patient, age 72, was treated with intracavernosal injections of the quadruple mix of the vasodilators prostaglandin E1, Atropine, Chlorpromazine and Papavarine on a regular basis (approximately two to four times per week) over a 3-month treatment. The indirect vasodilating effects of oral Cialis and Levitra were sometimes added to the quadruple mix of the vasodilators prostaglandin E1, Atropine, Chlorpromazine and Papavarine to produce and maintain a prolonged engorgement of 60-85% over a period of about 2.5 to 3 hours. The quantity of medication was adjusted in accordance with the patient's response. The potentiators Potaba 1000 mg 4×/day orally and prostaglandin F topically were also used with the vasodilators. After 3 months of treatment the patient's erect penis increased from 6.5 inches to 7.1 inches (about a 9% increase) in length.

EXAMPLE 8

A male patient, age 47, was treated with intracavernosal injections of a triple mix of the vasodilators Atropine, Chlorpromazine and Papavarine on a regular basis (approximately three to four times per week) over a 6-month treatment period. A sufficient quantity was administered to maintain a prolonged engorgement of an erectile response between 60-95% over a period of several hours, generally 3 to 4.5 hours. The quantity of medication was adjusted from time to time in accordance with the patient's response, which was monitored initially weekly. After 2 months of treatment subcutaneous injections of testosterone 14-20 mg into the penis were added as an accelerator.

The size of the patient's fully erect penis increased from 5.2 inches to 6.0 inches in length (about a 15% increase) over the 6 month treatment period.

EXAMPLE 9

A male patient, age 52, was treated with intracavernosal injections of the quadruple mix of the vasodilators prostaglandin E1, Atropine, Phentolamine and Papavarine on a regular basis (using IC medications approximately two to four days per week) over a 3-month treatment. Since the maximum duration of the engorgement of the erection from a single dose was only 45 to 80 minutes, the patient used two to three separate IC injects spaced through out the treatment days to achieve a total i.e. cumulative daily duration of 3 to 4 hours. The indirect vasodilating effects of oral Cialis and Levitra were sometimes added to the quadruple mix of the vasodilators prostaglandin E1, Atropine, Chlorpromazine and phentolamine to produce and maintain a prolonged engorgement of 60-85% over a period of about 3 to 4 hours. The quantity of medication was adjusted in accordance with the patient's response. The potentiator Potaba 1000 mg 4×/day orally was used with the vasodilator. After 4 months of treatment the patient's erect penis increased from 5.4 inches to 6.1 inches (about a 13% increase) in length and 4.4 to 5.1 inches in circumference (about a 16% increase in circumference).

EXAMPLE 10

A male patient, age 27, was treated with intracavernosal injections of a prostaglandin E1 on a regular basis (approximately two to five times per week) over a 3-month treatment period. Due to a sensitivity to Prostraglandin E1 causing aching and pain at higher doses, the maximum tolerated dose which produced a comfortable erection was only lasting 90 to 120 minutes. The patient used two separate IC injects spaced throughout the treatment days to achieve a total daily cumulative engorgement duration of 3 to 4 hours. The quantity of medication was adjusted in accordance with the patient's response. The 15 mg of the potentiator Dihydrotestosterone was injected subcutaenously into the penis daily throughout the treatment period. After 3 months of treatment the patient's erect penis increased from 6.3 inches to 7.1 inches (about an 13% increase) in length.

Although various examples of combined elements of the invention have been described, it will also be understood that these are not intended to be exhaustive and features of one embodiment may be combined with those of another, and such other combinations are contemplated to be within the scope of the invention disclosed herein.

All publications and other documents mentioned herein are hereby incorporated by reference into this specification.

While preferred embodiments of the invention have been illustrated and described, it will be appreciated that various changes and modifications can be made therein without departing from the spirit and scope of the invention as defined by the following claims.

The invention claimed is:

1. A method for causing a permanent increase in the length and girth of a male subject's penis, said method comprising the step of (a) administering to said male an effective amount of a vasodilator selected from the group consisting of papaverine, chlorpromazine, atropine, phentolamine, and prostaglandin E1, or a mixture thereof, and relaxin, which potentiates the effect of the vasodilator and compositions thereof comprising a pharmaceutically-acceptable diluent or carrier, to induce a cumulative prolonged engorgement of the subject's penis; and (b) repeating step (a) as necessary to cause said increase during said treatment.

2. A method as defined in claim 1, wherein said vasodilator is in admixture with a pharmaceutically-acceptable diluent or carrier, 3. A method as defined in claim 1, wherein said administration is such that said prolonged engorgement is sustained for at least 3.5 hours.

4. A method as defined in claim 3, wherein said prolonged engorgement is sustained for at least 4 hours.

5. A method as defined in claim 1, wherein said vasodilator is administered as one dose in said treatment step throughout the prolonged engorgement.

6. A method as defined in claim 1, wherein said vasodilator is administered as at least two doses as defined in said treatment throughout the prolonged engorgement.

7. A method as defined in claim 6, wherein the engorgement comprises a first erectile response of at least 65%, and a second dose or subsequent doses are administered after the first erectile response falls below 65% during said treatment.

8. A method as defined in claim 5 or claim 6, wherein said treatment is applied to said patient at least two times per week for a period of at least one month.

9. A method as defined in claim 8, wherein said treatment is applied to said patient at least four times per week for a period of at least 3 months.

10. A method as defined in claim 1, wherein the length of the fully erect penis has increased by at least 5% after a treatment period of 12 to 18 months.

11. A method as defined in claim 10, wherein the length of the fully erect penis is increased by at least 30% after a treatment period of 12 to 18 months.

12. A method as defined in claim 1, wherein the girth of the fully erect penis is increased by at least 5% after a treatment period of 12 to 18 months.

13. A method as defined in claim 12, wherein the girth of the fully erect penis is increased by at least 30% after a treatment period of 12 to 18 months.

14. A method as defined in claim 1, wherein said engorgement comprises a 75-100% erectile response for at least 90% of the time of the prolonged engorgement.

15. A method as defined in claim 1, wherein said engorgement comprises a 75-100% erectile response for 50-90% of the time of the prolonged engorgement.

16. A method as defined in claim 1, wherein said engorgement comprises a 75-100% erectile response for up to 50% of the time of the prolonged engorgement.

17. A method as defined in claim 1, wherein said engorgement comprises a 40-75% erectile response for at least 3 hours.

18. A method as defined in claim 1, wherein said vasodilator is prostaglandin E1.

19. A method as defined in claim 1, wherein said vasodilator is formulated for administration by direct injection to the cavernosal tissue, by needle, auto-injector, slow sustained injection pump, high pressure injection device, microinfusion pump, urethral suppository, or implantable sustained release drug or device.

20. A method as defined in claim 1, wherein said vasodilator is formulated for systemic administration by oral, sublingual, or suppository administration, intravenous administration by needle, auto-injector, slow sustained injection pump, high pressure injection device, microinfusion pump, or implantable sustained release drug or device, or topical administration, such as through the use of creams, lotions or patches.

21. A method as defined in claim 1, wherein said vasodilator is administered to the dense connective tissue surrounding the erectile tissue of the penis by a deep injection that goes below the dermis and subcutaneous tissues.

22. A method as defined in claim 1, wherein said vasodilator is administered as an intracavernosal injection.

23. A method as defined in claim 19, wherein said vasodilator is administered as an implantable sustained release drug or device.

24. A method as defined in claim 18, wherein said prostaglandin E1 is administered at a dosage of 0.5 to 100 micrograms/kg body weight/day by intracavernosal injection.

25. A method as defined in claim 18, wherein the prostaglandin E1 is administered systemically at a dosage of 2 to 10,000 microgramslkg body weight/day by an implantable sustained release drug or device.

26. A method as defined in claim 1, wherein the relaxin is administered by direct injection to the cavernosal tissue, by needle, auto-injector, slow sustained injection pump, high pressure injection device, microinfusion pump, urethral suppository, or implantable sustained release drug or device.

27. A method as defined in claim 1, wherein the relaxin is systemically administered by oral, sublingual, or suppository administration, intravenous administration by needle, auto-injector, slow sustained injection pump, high pressure injection device, microinfusion pump, or implantable sustained release drug or device, or topical administration, such as through the use of creams, lotions or patches.

28. A method as defined in claim 1, wherein the relaxin is administered to the dense connective tissue surrounding the erectile tissue of the penis by a deep injection that is well below the dermis and subcutaneous tissues.

29. A method as defined in claim 1, wherein the relaxin is administered by intracavernosal injection.

30. A method as defined in claim 1, wherein the relaxin is administered as an implantable sustained release drug or device.

31. A method as defined in claim 1, wherein the relaxin is administered separately from the composition.

32. A method as defined in claim 1, wherein the relaxin is administered concurrently with the composition.

33. A method as defined in claim 1, wherein the relaxin is administered more than once during said treatment.

34. A method as defined in claim 1, wherein relaxin is administered at a dosage of 0.02 to 1 micrograms/kg body weight/day by intracaversonal injection.

35. A method as defined in claim 1 wherein relaxin is topically administered at a dosage of 25 to 400 micrograms/kg body weight/day.

36. A method as defined in claim 1, wherein relaxin is administered at a dosage of 0.02 to 1 micrograms/kg body weight/day by injection into the dense connective tissue of the erectile tissue surrounding the penis.

37. A method as defined in claim 1, comprising applying a device to prolong the retention of the composition in the penis.

38. A method as defined in claim 37, comprising fitting said device in the form of a ring around the base of the penis.

* * * * *